United States Patent
Yang et al.

(10) Patent No.: US 11,166,462 B2
(45) Date of Patent: Nov. 9, 2021

(54) FUNGICIDAL COMPOUND, FUNGICIDE COMPOSITION AND PREPARATION AND USE THEREOF

(71) Applicant: Zhejiang Udragon Bioscience Co., Ltd., Zhejiang (CN)

(72) Inventors: Guangfu Yang, Hubei (CN); Hua Cheng, Hubei (CN); Hualong Wu, Zhejiang (CN)

(73) Assignee: ZHEJIANG UDRAGON BIOSCIENCE CO., LTD., Jiaxing (CN)

( * ) Notice: Subject to any disclaimer, the term of this patent is extended or adjusted under 35 U.S.C. 154(b) by 502 days.

(21) Appl. No.: 16/068,071

(22) PCT Filed: Nov. 2, 2016

(86) PCT No.: PCT/CN2016/104314
§ 371 (c)(1),
(2) Date: Jul. 3, 2018

(87) PCT Pub. No.: WO2017/118193
PCT Pub. Date: Jul. 13, 2017

(65) Prior Publication Data
US 2020/0275658 A1  Sep. 3, 2020

(30) Foreign Application Priority Data
Jan. 5, 2016 (CN) .......................... 201610003201.6

(51) Int. Cl.
*A01N 43/653* (2006.01)
*C07D 249/12* (2006.01)

(52) U.S. Cl.
CPC ......... *A01N 43/653* (2013.01); *C07D 249/12* (2013.01)

(58) Field of Classification Search
CPC ............................. A01N 43/653; C07D 249/12
See application file for complete search history.

(56) References Cited

U.S. PATENT DOCUMENTS

| | | | |
|---|---|---|---|
| 5,527,818 A | 6/1996 | Atsushi | |
| 6,620,812 B2 | 9/2003 | Takeyama | |
| 2014/0128255 A1 | 5/2014 | Dietz | |
| 2014/0141973 A1 | 5/2014 | Dietz | |
| 2014/0187422 A1 | 7/2014 | Dietz | |
| 2015/0284344 A1 | 10/2015 | Grammenos | |
| 2015/0307459 A1 | 10/2015 | Grammenos | |
| 2015/0351399 A1 | 12/2015 | Grammenos | |
| 2016/0002179 A1 | 1/2016 | Grammenos | |
| 2017/0081296 A1 | 3/2017 | Dietz | |

FOREIGN PATENT DOCUMENTS

| | | | |
|---|---|---|---|
| AU | 2407797 A | 11/1997 | |
| CN | 1279679 A | 1/2001 | |
| CN | 1401648 A | 3/2003 | |
| CN | 101928253 A | 12/2010 | |
| CN | 103648281 A | 3/2014 | |
| CN | 103649057 A | 3/2014 | |
| CN | 103649058 A | 3/2014 | |
| CN | 103717579 A | 4/2014 | |
| CN | 104903315 A | 9/2015 | |
| CN | 104955814 A | 9/2015 | |
| CN | 105008332 A | 10/2015 | |
| CN | 105008336 A | 10/2015 | |
| CN | 105130917 A | 12/2015 | |
| CN | 105669576 A | 6/2016 | |
| CN | 105693638 A | 6/2016 | |
| JP | 1992297464 A | 10/1992 | |
| JP | 1993004976 A | 1/1993 | |
| JP | 1993140124 A | 6/1993 | |
| WO | 199741113 A1 | 11/1997 | |
| WO | 2015185708 A1 | 12/2015 | |

OTHER PUBLICATIONS

Fungicidal activity of triazole compounds and plant growth regulation, Bai Lin et al., Journal of Gansu Normal Colleges, vol. 5 No. 2(2000): 51-55.
Synthesis and Fungicidal Activities of Novel Analogues of Strobilurins Containing 1,2,4-Triazol Moiety, Zhao Peiliang et al., Chinese Journal of Organic Chemistry, vol. 28, No. 5, May 2008: 875-880.
Research progress on fungicidal activity of 1,2,4-triazole compounds, Jiangsu Agricultural Science, Aug. 2013, 41 (8): 134-137.
Derivatives of 7-methyl-6-thia-1,6-dihydro- and 7-methyl-6-thia-1,2,3,6-tetrahydropurine 6,6-dioxide, F. F. Blicke and C. Lee, Journal of Organic Chemistry, 1961, vol. 26: 1861-1867.

*Primary Examiner* — Sue X Liu
*Assistant Examiner* — Andriae M Holt
(74) *Attorney, Agent, or Firm* — Volpe Koenig

(57) ABSTRACT

The present invention relates to the field of agricultural fungicides, and discloses a compound with fungicidal activity, a fungicide composition and a preparation using the compound as an active ingredient, and a use thereof. The structure of the fungicidal compound is represented by formula (I) or formula (II). The fungicidal compound and the preparation containing the fungicidal compound in the present invention can achieve a remarkable prevention and control effect against cucumber downy mildew and rice sheath blight.

14 Claims, No Drawings

FUNGICIDAL COMPOUND, FUNGICIDE COMPOSITION AND PREPARATION AND USE THEREOF

CROSS REFERENCE TO RELATED APPLICATIONS

This application is a 35 USC § 371 national stage application of PCT/CN2016/104314, which was filed Nov. 2, 2016 and claimed priority to CN 201610003201.6, filed Jan. 5, 2016, both of which are incorporated herein by reference as if fully set forth.

FIELD OF THE INVENTION

The present invention relates to the field of agricultural fungicides, specifically relates to a compound with fungicidal activity, and a fungicide composition and a preparation using the compound as an active ingredient, particularly relates to a compound for preventing and controlling cucumber downy mildew and rice sheath blight, a fungicide composition and a preparation containing the compound, and a use thereof.

BACKGROUND OF THE INVENTION

Cucumber downy mildew is harmful to both seedlings and adult plants, and mainly causes harms to leaves and stems and less harms to tendrils and peduncles. Cucumber downy mildew is the most common and the most harmful disease occurring in cucumber cultivation in protected areas. The disease is acute, heavy and spread rapidly, and may cause a devastating loss to cucumbers if it is not prevented and controlled timely. The pathogen of cucumber downy mildew is *Pseudoperonospora cubensis* in the genus *Pseudoperonospora*, the subphylum Mastigomycotina, and the sporangia of the pathogen spread in air flow and rainwater. In green houses, the production activities of human are the main source of infection of downy mildew. Cucumber downy mildew outbreaks the most easily at 16-24° C. temperature, is hard to outbreak at temperatures lower than 10° C. or higher than 28° C., and seldom occurs at temperatures lower than 5° C. or higher than 30° C. Cucumber downy mildew may outbreak easily when the humidity is 85% or higher; especially, cucumber leaves covered by a water film may be infected by cucumber downy mildew the most easily. The spores of the pathogen are hard to germinate when the humidity is lower than 70%, and can't be formed when the humidity is lower than 60%. The pathogen survives in the protected area, and spreads in spring in the next year; or the pathogen may spread with the monsoon from southern regions. The pathogen may spread in air flow and rainwater in summer. In northern regions, cucumber downy mildew spreads from green houses to plastic greenhouse, then spreads to ridge cucumbers in spring and to ridge cucumbers in autumn, and finally returns to cucumbers in green houses. The pathogen is an obligatory parasitic fungus to the living plant and doesn't infect the seeds. It mainly spreads in air flow and intrudes into cucumbers through the leaf stomas.

To effectively prevent and control cucumber downy mildew, a novel fungicidal compound that can achieve a remarkable cucumber downy mildew prevention and control effect is required.

Contents of the Invention

The object of the present invention is to provide a novel fungicidal compound that can attain a remarkable plant disease prevention and control effect, a fungicide composition and a preparation containing the fungicidal compound, and a use of the fungicide composition and the preparation, in particular a novel fungicidal compound that can achieve a remarkable prevention and control effect against cucumber downy mildew, a fungicide composition and a preparation containing the fungicidal compound, and a use of the fungicide composition and the preparation.

According to a first aspect of the present invention, the present invention provides a fungicidal compound in a structure represented by formula (I) or (II):

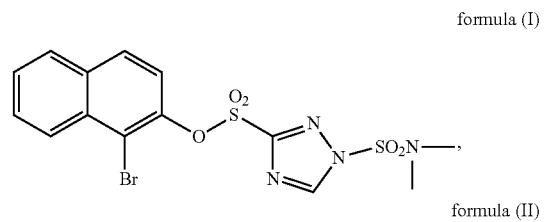

formula (I)

formula (II)

According to a second aspect of the present invention, the present invention provides a fungicide composition, wherein the active ingredient comprises a compound in a structure represented by formula (I) and/or formula (II):

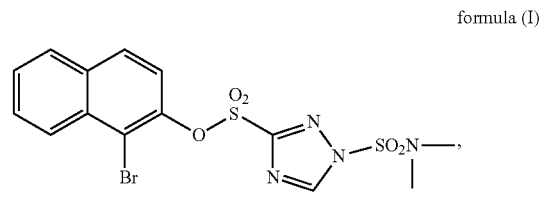

formula (I)

formula (II)

According to a third aspect of the present invention, the present invention provides a use of the fungicide composition in prevention and control of cucumber downy mildew and/or rice sheath blight.

According to a fourth aspect of the present invention, the present invention provides a preparation prepared from the fungicide composition, wherein the formulation of the preparation is emulsifiable concentrate, aqueous emulsion, microemulsion, soluble liquid, water suspension, suspension emulsion, ultra low volume spray, oil suspension, microcapsule suspension, surface spreading oil, wettable powder, water dispersible granule, dry flowable, soluble powder, soluble granule, emulsifiable powder, emulsifiable granule, pelletized granule, solid micro-capsule, effervescent tablet, effervescent granule, water floating dispersible granule, or seed coating agent.

According to a fourth aspect of the present invention, the present invention provides a use of the preparation in prevention and control of cucumber downy mildew and/or rice sheath blight.

The compound provided in the present invention can achieve a remarkable prevention and control effect against plant diseases, particularly against cucumber downy mildew.

Other features and advantages of the present invention will be further detailed in the embodiments hereunder.

DETAILED DESCRIPTION OF THE EMBODIMENTS

Hereunder some embodiments of the present invention will be detailed. It should be understood that the embodiments described here are only provided to describe and explain the present invention, but shall not be deemed as constituting any limitation to the present invention.

The structure of the fungicidal compound provided in the present invention is represented by formula (I) or (II):

formula (I)

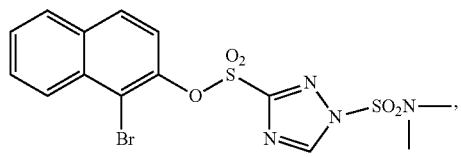

formula (II)

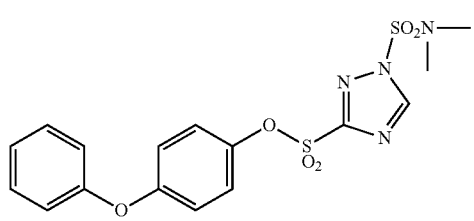

The active ingredient in the fungicide composition provided in the present invention comprises a compound in a structure represented by formula (I) and/or (II):

formula (I)

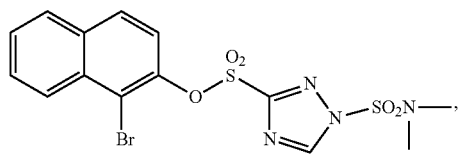

formula (II)

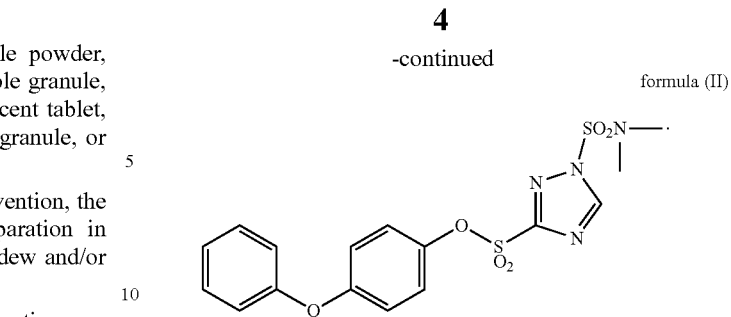

The compound represented by formula (I) (hereinafter also referred to as Y14078) in the present invention may be synthesized through a synthetic route represented by the following synthetic route (1):

Synthetic Route (1)

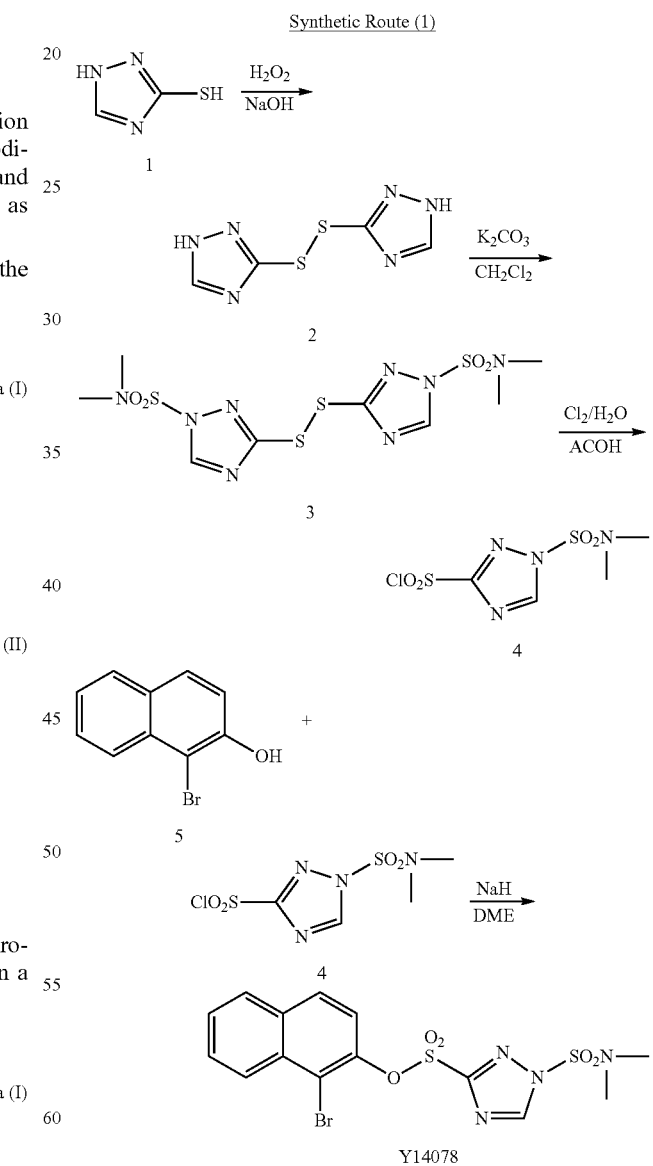

The compound represented by formula (II) (hereinafter also referred to as Y14079) in the present invention may be synthesized through a synthetic route represented by the following synthetic route (2):

Synthetic Route (2)

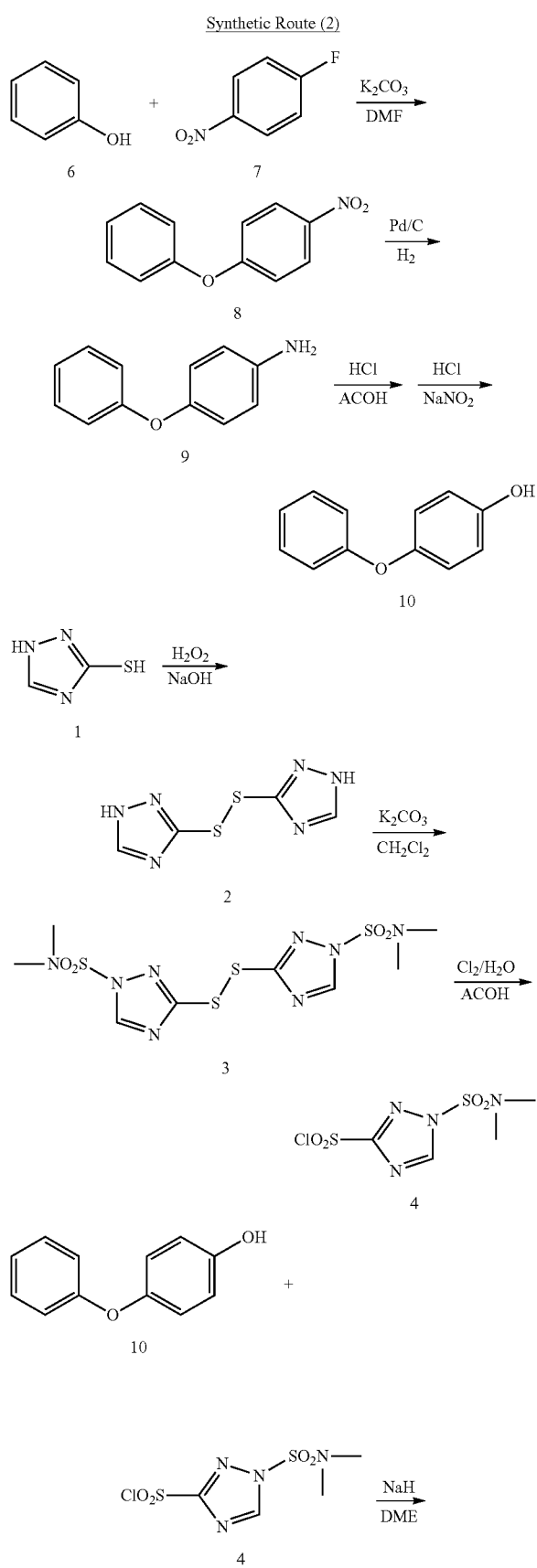

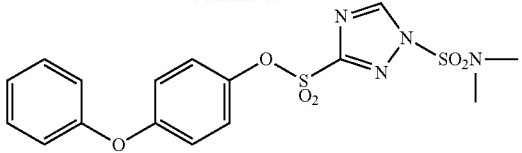

Y14079

In the fungicide composition provided in the present invention, the content of the active ingredient in the fungicide composition may vary within a wide range. Specifically, the content of the active ingredient in the composition is 1-95 wt %, preferably is 5-80 wt %, and further preferably is 30-60 wt %.

Besides the active ingredient, the fungicide composition provided in the present invention usually further comprises surfactant(s) and carrier(s) acceptable in pesticide science.

The surfactant may be any surfactant well known in the pesticide formulation field, and preferably is one or more of emulsifier, disperser, and wetter in the present invention.

The other carrier excluding the surfactant may be any carrier well known in the pesticide formulation field, including silicates, carbonates, sulfates, oxides, phosphates, plant carriers, and synthetic carriers, etc. Specifically, for example, the carrier may be one or more of white carbon black, kaolin, kieselguhr, clay, talcum, organic bentonite, pumice, titanium dioxide, dextrin, cellulose powder, light calcium carbonate, soluble starch, maize starch, sawdust powder, urea, amine, mixture of urea and amine, glucose, maltose, sucrose, anhydrous potassium carbonate, anhydrous sodium carbonate, anhydrous potassium bicarbonate, anhydrous sodium bicarbonate, attapulgite clay, mixture of anhydrous potassium carbonate and anhydrous potassium bicarbonate, and mixture of anhydrous sodium carbonate and anhydrous sodium bicarbonate.

The emulsifier may be any emulsifier well known in the pesticide formulation field. Specifically, the emulsifier may be one or more of calcium dodecyl benzene sulfonate, triphenylethyl phenol polyoxyethylene ether phosphate, fatty alcohol polyoxyethylene ether, alkylphenol polyoxyethylene ether, alkylphenol polyoxyethylene polyoxypropylene ether, fatty amine, ethylene oxide adduct of fatty amide, polyoxyethylene fatty acid ester, abietic acid ethylene oxide adduct, polyol fatty acid ester and ethylene oxide adduct of polyol fatty acid ester, styryl phenyl polyoxyethylene ether, alkylphenol formaldehyde resin polyoxyethylene ether, hydroxyl-terminated polyoxyethylene polyoxypropylene ether, styrylphenol formaldehyde resin polyoxyethylene polyoxypropylene ether, and castor oil polyoxyethylene ether.

The disperser(s) may be any disperser well known in the pesticide formulation field. Specifically, the disperser may be one or more of sodium polyacrylate, disodium maleate, sodium salt of naphthalene sulfonic acid-formaldehyde condensate, rosin-blocked polyoxyethylene ether polyoxypropylene ether sulfonate, hydroxyl-terminated polyoxyethylene polyoxypropylene ether block copolymer, triphenylethyl phenol polyoxyethylene ether phosphate, fatty alcohol polyoxyethylene ether phosphate, and p-hydroxyphenyl sodium lignosulfonate.

The wetter may be any wetter well known in the pesticide formulation field. Specifically, the wetter may be one or more of sodium dodecyl sulfate, sec-alkyl sodium sulfate, sodium dodecyl benzene sulfonate, fatty alcohol polyoxyethylene ether, alkyl-naphthalene sulfonate, and alkylphenol resin polyoxyethylene ether sulfate.

The fungicide composition provided in the present invention may contain various common additives for preparations in the pesticide formulation field. Specifically, the additives for preparations may be one or more of solvent, solubilizer, thickener, anti-freezer, capsule wall material, protectant, anti-foamer, disintegrant, stabilizer, preservative, and binder.

The solvent may be any solvent well known in the pesticide formulation field. Specifically, the solvent may be one or more of organic solvent, vegetable oil, mineral oil, solvent oil, and water.

Wherein, the organic solvent comprises one or more of N-methyl pyrrolidone, tetrahydrofuran, dimethyl sulfoxide, N,N-dimethyl decylamide, N,N-dimethyl formamide, trimethyl benzene, tetramethyl benzene, dimethyl benzene, methyl benzene, octane, heptane, methanol, isopropanol, n-butanol, tetrahydrofurfuryl alcohol, tributyl phosphate, 1,4-dioxane, and cyclohexanone.

The vegetable oil comprises one or more of methylated vegetable oil, rosin-based vegetable oil, turpentine, epoxy soybean oil, soybean oil, peanut oil, colza oil, castor oil, maize oil, and pine seed oil.

The mineral oil comprises one or more of liquid wax, engine oil, kerosene, and lubricant oil.

In addition, the above-mentioned solvent may also be used as a solubilizer.

The anti-freezer may be any anti-freezer well known in the pesticide formulation field, and preferably is one or more of ethylene glycol, propylene glycol, glycerol and urea in the present invention.

The thickener may be any thickener well known in the pesticide formulation field. Specifically, the thickener may be one or more of xanthan gum, polyvinyl alcohol, polypropylene alcohol, polyethylene glycol, white carbon black, kieselguhr, kaolin, clay, sodium alginate, magnesium aluminum silicate, sodium aluminosilicate, carboxymethyl cellulose, sodium hydroxypropyl cellulose, and organophilic bentonite.

The capsule wall material may be any capsule wall material well known in the pesticide formulation, and preferably is one or more of polyurethane, polyurea, and urea-formaldehyde resin in the present invention.

The protectant may be any protectant well known in the pesticide formulation field, and preferably is polyvinyl alcohol and/or polyethylene glycol in the present invention.

The anti-foamer may be any anti-foamer well known in the pesticide formulation field, and preferably is one or more of organo-siloxane, tributyl phosphate and silicone.

The stabilizer is selected from one or more of triphenyl phosphite, epoxy chloropropane, and acetic anhydride.

The preservative is selected from one or more of benzoic acid, sodium benzoate, 1,2-benzo-isothiazolin-3-ketone (abbreviated as BIT), Kathon and potassium sorbate.

The present invention further provides a use of the fungicide composition in prevention and control of cucumber downy mildew and/or rice sheath blight.

The present invention further provides a preparation prepared from the fungicide composition, wherein the formulation of the preparation is emulsifiable concentrate, aqueous emulsion, microemulsion, soluble liquid, water suspension, suspension emulsion, ultra low volume spray, oil suspension, micro-capsule suspension, surface spreading oil, wettable powder, water dispersible granule, dry flowable, soluble powder, soluble granule, emulsifiable powder, emulsifiable granule, pelletized granule, solid micro-capsule, effervescent tablet, effervescent granule, water floating dispersible granule, or seed coating agent. All of the above-mentioned formulations can be prepared with conventional methods in the art.

Preferably, measured in weight percentage, the emulsifiable concentrate preparation consists of 1-95% active ingredient, 0-20% solubilizer, 1-'30% emulsifier, and solvent that accounts for the remaining content to make up to 100%.

For example, the method for preparing the emulsifiable concentrate preparation may comprise mixing the active ingredient, solvent, solubilizer and emulsifier while stirring to form a homogenous and clear oil phase; thus, the emulsifiable concentrate preparation is obtained.

Preferably, measured in weight percentage, the aqueous emulsion or microemulsion consists of 1-95% active ingredient, 1-30% emulsifier, 0-30% solubilizer, 1-30% solvent, 0-10% anti-freezer, 0-10% thickener, and water that accounts for the remaining content to make up to 100%.

Preferably, for example, the method for preparing the aqueous emulsion may comprise: mixing the active ingredient, emulsifier, solubilizer and solvent to form a homogenous oil phase; mixing the water, thickener, and anti-freezer to form a homogenous water phase; and adding the water phase into the oil phase or adding the oil phase to the water phase under a high-speed shearing condition, to form well-dispersed aqueous emulsion.

Preferably, the method for preparing the microemulsion comprises: mixing the active ingredient, emulsifier, and solvent while stirring to form a homogenous and clear oil phase; adding water gradually while stirring, to form homogenous and clear micro-emulsion.

Preferably, measured in weight percentage, the water suspension consists of 1-95% active ingredient, 1-30% surfactant, 1-10% anti-freezer, 0.1-5% thickener, and water that accounts for the remaining content to make up to 100%.

Preferably, measured in weight percentage, the oil suspension consists of 1-95% active ingredient, 1-30% emulsifier, 0.1-10% disperser, 0.1-5% thickener, and oil that accounts for the remaining content to make up to 100%.

Method for preparing the water/oil suspension: utilizing water or oil as a medium, adding the active ingredient and additives (e.g., surfactant, etc.) into a grinding kettle, grinding the mixture to certain granule size, filtering, and then adding a weighed thickener into the ground mother liquid, and shearing and dispersing the mixture to a homogeneous state, so as to obtain the oil suspension or water suspension.

Preferably, measured in weight percentage, the soluble granule, soluble powder, water dispersible granule, or wettable powder consists of 1-95% active ingredient, 1-30% surfactant, and other carrier that accounts for the remaining content to make up to 100%.

Wherein, the method for preparing the water dispersible granule and soluble granule comprises: mixing the active ingredient, disperser, wetter, and carrier, etc., to a homogenous state, and then pulverizing the mixture to certain granule size by means of air flow, adding water and kneading, and finally loading the mixture into a pelletizer and pelleting, and then drying, so as to obtain the water dispersible granule or soluble granule.

The method for preparing the soluble powder and wettable powder comprises: mixing the active ingredient, additives, and other carrier intensively, and then pulverizing with a super-fine pulverizer.

The present invention further provides a use of the preparation in prevention and control of cucumber downy mildew and/or rice sheath blight.

The fungicide composition provided in the present invention may be supplied in the form of a finished preparation product, i.e., the substances in the composition have been mixed well; or the fungicide composition may be supplied in the form of separate preparations, which may be mixed in a barrel or tank by the user and then the mixture may be diluted with water selectively by the user according to the required concentration of the active substance before use.

Furthermore, the composition provided in the present invention may be used in mixture with other compounds that have fungicidal, pesticidal, or herbicidal capability, or may be used in mixture with nemacides, protectants, growth regulators, plant nutrients, or soil conditioners, etc.

The fungicide composition provided in the present invention is easy and simple to use. Specifically, it may be applied to the plant and plant growth location in a conventional way, such as puddling, spraying, jetting, or pouring, etc., before or after the plant disease appears; the amount of use may be determined according to the climatic conditions or the state of the plant, usually 10-5,000 g may be applied per mu, by diluting to 10-400 mg/L (preferably 100-300 mg/L) concentration. The diluent preferably is water.

The fungicidal effect of the fungicide composition provided in the present invention is usually related with environmental factors (e.g., weather conditions), but the influence of weather conditions may be mitigated by using an appropriate formulation.

Hereunder the present invention will be further detailed in specific embodiments, but the present invention is not limited to the embodiments described below.

In the following preparation examples, the percentage contents in the mix ratios of all preparations are weight percentages.

In the following test cases and preparation examples, the compound represented by formula (I) is synthesized through the above-mentioned synthetic route (1), and the specific synthesis method is as follows.

(1) Synthesis of Compound 2

1.01 g (10 mmol) 3-sulfhydryl-1,2,4-triazole (compound 1) is dissolved in 5 mL methylene chloride, and then 0.79 g (10 mmol) redistilled pyridine is added. Under the conditions of ice-water bath and stirring, 0.88 g (5 mmol) benzene sulfonyl chloride is added by dropwise adding in 1 h. The ice-water bath is removed, and the mixture is stirred for 16 h at room temperature. The methylene chloride is evaporated, and 5 mL water and 3 mL ethyl acetate are added to the remaining mixture under a mechanical stirring condition, and the mixture is held for 1 h for reaction. Next, the product is filtered, and the filter residue is washed with 20 mL water and 20 mL ethyl acetate respectively. Then, the obtained product is dried under a vacuum condition at 60-70° C.; thus, 0.92 g compound 2 is obtained, and the yield ratio is 92%.

(2) Synthesis of Compound 3

0.6 g (1 mmol) compound 1 is mixed with 15 mL N,N-dimethyl formamide (DMF) and 0.828 g potassium carbonate while stirring, and then the mixture is heated up to 30° C. The temperature is controlled at 28-32° C., 0.951 g N,N-dimethyl sulfuryl chloride is added by dropwise adding in 2 h, and the mixture is held for 6 h for reaction; after the reaction, 90 mL 1,2-dichloroethane is added, and then 30 mL 35% hydrochloric acid and 120 mL water are poured to the mixture, and the temperature is kept at 20° C.-25° C. The organic phase is separated; the obtained product contains 1.119 g compound 3, and the yield ratio is 90%.

(3) Synthesis of Compound 4

20 mL water is added into 10 mL 1,2-dichloroethane that contains 0.829 g (2 mmol) compound 3, the mixture is cooled to 0° C., 10 mL acetic acid is added, then the temperature is controlled at 15° C.-20° C., 0.781 g (11 mmol) chlorine is charged into the mixture, and the mixture is held for half hour for reaction. After the reaction, the solution is transferred into a separating funnel, and is held in still for separation; the obtained organic phase is washed with 30 mL for three times, and then the solvent is evaporated; thus, 0.997 g compound 4 is obtained, and the yield ratio is 91%.

(4) Synthesis of Target Compound Y14078

0.1 mmol 1-bromo-2-naphthol (compound 5) and 0.2 mmol NaOH (at 60% purity) are stirred in dry ethylene glycol dimethyl ether (DME) for 1 h; under an ice bath condition, DME mixed solution in which 0.1 mmol compound 4 is dissolved is added by dropwise adding, and then the mixture is held at room temperature for reaction. After the reaction, some water is added to quench the reaction, and then the product is extracted with methylene chloride, the obtained organic phase is dried with anhydrous sodium sulfate; thus, the target compound Y14078 is obtained.

The obtained Y14078 is white solid, M.p.157-158° C.; $^1$H NMR (600 MHz, DMSO-$d_6$) δ 9.66 (s, 1H), 8.10 (d, J=8.0 Hz, 1H), 7.99 (d, J=8.8 Hz, 1H), 7.82 (d, J=8.8 Hz, 1H), 7.77 (d, J=8.0 Hz, 1H), 7.72-7.62 (m, 2H), 2.96 (s, 6H). $^{13}$C NMR (100 MHz, DMSO-$d_6$) δ 158.71, 149.02, 142.55, 133.32, 129.81, 129.52, 128.34, 128.30, 127.90, 127.53, 120.90, 113.86, 38.36. EI-MS: m/z=460.08 Anal. Calcd for $C_{14}H_{13}BrN_4O_5S_2$ (461.95): C, 36.45; H, 2.84; N, 12.15; S, 13.90. Found: C, 36.75; H, 2.649; N, 11.93; S, 13.61.

In the following test cases and preparation examples, the compound represented by formula (II) is synthesized through the above-mentioned synthetic route (2), and the specific synthesis method is as follows.

(1) Synthesis of Compound 8

Under nitrogen shielding, 1.0 mmol compound 7, 1.1 mmol compound 5, and 1.5 mmol $K_2CO_3$ are added into a three-necked bottle filled with 5 mL DMF, the mixture is held in oil bath (at 60° C. temperature) for 8 h for reaction, and the reaction process is monitored with a TLC. After the reaction, the system is cooled to room temperature, and the product is poured into ice water; as a result, a great deal of precipitate occurs; the mixture is held in a still state for stratification, and then is filtered; thus, a compound 8 (1-nitro-4-phenoxybenzene) is obtained.

(2) Synthesis of Compound 9

5 mmol compound 8 is dissolved in 25 mL methylene chloride, 10% Pd—C is added (the mass of Pd—C is 15% of the mass of the compound 8), $H_2$ is charged, and the reaction process is monitored with a TLC, the reaction time is usually 30 minutes; after the reaction, the product is filtered, and the solvent is removed from the filtrate, to obtain a crude product; thus, a compound 9 (1-amino-4-phenoxybenzene) is obtained.

(3) Synthesis of Compound 10

Under nitrogen shielding, 0.4 mmol compound 9 is dissolved in 3 mL glacial acetic acid, and then the solution is heated up slowly to 50-55° C.; after the solution becomes clear, 3.5 mL 2N hydrochloric acid solution is added slowly by dropwise adding; then 3 mL 2N sodium nitrite solution is added under an ice bath condition; after the reaction mixture becomes clear, 1 mL 38% fluoboric acid solution is added, and then the mixture is held at 80° C. for 4 h for reaction. After the reaction is completed, the system is cooled to room temperature; as a result, a great deal of precipitate is produced; the mixture is filtered, the filter residue is dissolved in 3 mL acetic anhydride under a nitrogen shielding condition, and then is heated up to 110° C. and held for 3 h at the temperature for reaction; next, excessive acetic anhydride is removed by depressurization, and then 4 mL ethanol and 1 mL 45% NaOH solution are added, and the mixture is heated and held for 2 h for reflux reaction; then, 2N hydrochloric acid is added to adjust the pH to about 6; finally, the product is extracted with ethyl acetate and then washed with saturated saline solution, dried with anhydrous sodium sulfate, filtered, and desolventized; thus, a compound 10 is obtained.

(4) Synthesis of Compound 2

1.01 g (10 mmol) 3-sulfhydryl-1,2,4-triazole (compound 1) is dissolved in 5 mL methylene chloride, and then 0.79 g (10 mmol) redistilled pyridine is added. Under the conditions of ice-water bath and stirring, 0.88 g (5 mmol) benzene sulfonyl chloride is added by dropwise adding in 1 h. The ice-water bath is removed, and the mixture is stirred for 16 h at room temperature. The methylene chloride is evaporated, and 5 mL water and 3 mL ethyl acetate are added to the remaining mixture under a mechanical stirring condition, and the mixture is held for 1 h for reaction. Next, the product is filtered, and the filter residue is washed with 20 mL water and 20 mL ethyl acetate respectively. Then, the obtained product is dried under a vacuum condition at 60-70° C.; thus, 0.92 g compound 2 is obtained, and the yield ratio is 92%.

(5) Synthesis of Compound 3

0.6 g (1 mmol) compound 1 is mixed with 15 mL DMF and 0.828 g potassium carbonate while stirring, and then the mixture is heated up to 30° C. The temperature is controlled at 28-32° C., 0.951 g N,N-dimethyl sulfuryl chloride is added by dropwise adding in 2 h, and the mixture is held for 6 h for reaction; after the reaction, 90 mL 1,2-dichloroethane is added, and then 30 mL 35% hydrochloric acid and 120 mL water are poured to the mixture, and the temperature is kept at 20° C.-25° C. The organic phase is separated; then obtained product contains 1.119 g compound 3, and the yield ratio is 90%.

(6) Synthesis of Compound 4

20 mL water is added into 10 mL 1,2-dichloroethane that contains 0.829 g (2 mmol) compound 3, the mixture is cooled to 0° C., 10 mL acetic acid is added, then the temperature is controlled at 15° C.-20° C., 0.781 g (11 mmol) chlorine is charged into the mixture in 3 h, and the mixture is held for half hour for reaction. After the reaction, the solution is transferred into a separating funnel, and is held in still for separation; the obtained organic phase is washed with 30 mL for three times, and then the solvent is evaporated; thus, 0.997 g compound 4 is obtained, and the yield ratio is 91%.

(7) Synthesis of Target Compound Y14079

0.1 mmol compound 10 and 0.2 mmol NaH (at 60% purity) are stirred in dry DME for 1 h; under an ice bath condition, DME mixed solution in which 0.1 mmol compound 4 is dissolved is added by dropwise adding, and then the mixture is held at room temperature for reaction. After the reaction, some water is added to quench the reaction, and then the product is extracted with methylene chloride, the obtained organic phase is dried with anhydrous sodium sulfate; thus, the target compound Y14079 is obtained.

The obtained compound Y14079 is colorless solid, M.p.141-143° C. $^1$H NMR (600 MHz, DMSO-$d_6$) δ 9.57 (s, 1H), 7.45 (dt, J=14.5, 8.3 Hz, 3H), 7.23 (d, J=7.4 Hz, 1H), 7.05-7.01 (m, 3H), 7.01-6.97 (m, 2H), 6.78 (t, J=2.3 Hz, 1H), 2.92 (s, 6H). $^{13}$C NMR (100 MHz, DMSO-$d_6$) δ 157.96, 156.23, 155.85, 144.04, 130.21, 124.18, 123.70, 119.38, 119.17, 38.27. EI-MS: m/z=424.06 Anal. Calcd for $C_{16}H_{16}N_4O_6S_2$ (424.05): C, 45.28; H, 3.80; N, 13.20; S, 15.11. Found: C, 45.50; H, 4.038; N, 12.93; S, 15.27.

Test Case 1

Test Object: *Pseudoperonospora cubensis*

Test design: the compound in a structure expressed by formula (I) (Y14078), the compound in a structure expressed by formula (II) (Y14079), and a reference chemical amisulbrom are prepared with DMF into 5% emulsifiable concentrate (hereafter abbreviated as EC) respectively, and then the EC is diluted with water containing 1% Tween 80 to 5 concentration gradients, i.e., 100, 50, 25, 12.5, and 6.25 mg/L. Each process is repeated for 4 times.

Test method: the biological activity of the formulation is measured with a spore suspension spray inoculation method. Pot-cultured cucumber seedlings in the same growth state in the 1-leaf and 1-heart stage (with the growing point removed) are selected, sprayed with the formulation, and dried naturally. After 24 h, spores on the back side of the leaf infected by the disease is picked with a writing brush dipped with distilled water, and are prepared into spore suspension (2-3×$10^5$ spores/ml), the spore suspension is sprayed uniformly with an inoculating sprayer (at 0.1 MPa pressure) to the leaves of cucumbers, and then the inoculated cucumber seedlings are moved into a climatic chamber (relative humidity: 100%, temperature: 20° C., light-dark cycle time: 14 h/10 h) and cultured. After 24 h, the relative humidity is maintained at about 90% for induction; after 5 d, grading and investigation are carried out on the basis of the disease situation of the blank control group, and the control effect (%) is calculated according to the disease severity index.

Investigation Method and Grading Criteria:

Level 0: free from disease;

Level 1: disease speckle area accounts for 5% or less of the total area of the leaf;

Level 3: disease speckle area accounts for 6%-10% of the total area of the leaf;

Level 5: disease speckle area accounts for 11%-25% of the total area of the leaf;

Level 7: disease speckle area accounts for 26%-50% of the total area of the leaf;

Level 9: disease speckle area accounts for 50% or more of the total area of the leaf.

Effect Calculation:

Disease index=Σ(quantity of leaves at all levels× relative level value)×100/(total quantity of leaves×9);

Control effect (%)=(disease index of the control group−disease index of treated group)×100/ disease index of control group The results are shown in Table 1.

TABLE 1

| No. | Concentration (mg/L) | Control effect (%) | Regression curve (A + BX) | $EC_{50}$ (mg/L) | Relevance coefficient R | 95% confidence interval |
|---|---|---|---|---|---|---|
| Formula (I) | 100 | 87.58 | 3.6419 + 1.249 8X | 12.21 | 0.99 | 8.81~15.58 |
|  | 50 | 76.24 |  |  |  |  |
|  | 25 | 67.27 |  |  |  |  |
|  | 12.5 | 49.97 |  |  |  |  |
|  | 6.25 | 35.56 |  |  |  |  |
| Formula (II) | 100 | 94.63 | 3.0631 + 1.709 9X | 13.57 | 0.99 | 10.81~16.32 |
|  | 50 | 85.56 |  |  |  |  |
|  | 25 | 59.89 |  |  |  |  |
|  | 12.5 | 47.79 |  |  |  |  |
|  | 6.25 | 31.21 |  |  |  |  |

Test Case 2

Test Object: *Pseudoperonospora cubensis, Rhizoctonia Solani*

Test design: the compound in a structure expressed by formula (I) (Y14078) and the compound in a structure expressed by formula (II) (Y14079) are prepared with DMF into 5% emulsifiable concentrate (hereafter abbreviated as EC) respectively, and then the EC is diluted with water containing 1% Tween 80 to prepare 200 mg/L formulation. Each process is repeated for 4 times.

Test method for *Pseudoperonospora cubensis*: the biological activity of the formulation is measured with a spore suspension spray inoculation method. Pot-cultured cucumber seedlings in the same growth state in the 1-leaf and 1-heart stage (with the growing point removed) are selected, sprayed with the formulation, and dried naturally. After 24 h, spores on the back side of the leaf infected by the disease is picked with a writing brush dipped with distilled water, and are prepared into spore suspension (2-3×10⁵ spores/nil), the spore suspension is sprayed uniformly with an inoculating sprayer (at 0.1 MPa pressure) to the leaves of cucumbers, and then the inoculated cucumber seedlings are moved into a climatic chamber (relative humidity: 100%, temperature: 20° C., light-dark cycle time: 14 h/10 h) and cultured. After 24 h, the relative humidity is maintained at about 90% for induction; after 5 d, grading and investigation are carried out on the basis of the disease situation of the blank control group, and the control effect (%) is calculated according to the disease severity index.

Test method for *Rhizoctonia solani*: two pot-cultured seedlings in the same growth state in the true leaf stage are selected, sprayed with the formulation and then dried, and fungus cakes are attached to the leaves with the hypha side facing the leave. The seedlings are kept in a dark environment at 22-26° C. moisturizing for 24 h, and then the natural lighting is recovered, and the seedlings are cultured for about 4 days. After the disease is developed extensively in the control group, the diameter of the disease speckle at each inoculated site is measured with callipers, and the control effect is calculated.

The investigation method and grading criteria are the same as those in the test case 1, and the results are shown in Table. 2.

TABLE 2

| | | Control effect (%) | |
|---|---|---|---|
| No. | Concentration (mg/L) | Rice sheath blight | Cucumber downy mildew |
| Y14078 | 200 | 52.5 | 100 |
| Y14079 | 200 | 67.5 | 100 |

It is seen from the above Table 1: The $EC_{50}$ values against cucumber downy mildew of Y14078 and Y14079 are 12.21 and 13.57 respectively, which indicate remarkable control effects against cucumber downy mildew. It is seen from Table 2: at 200 mg/L concentration, both Y14078 and Y14079 achieve a good control effect against rice sheath blight and cucumber downy mildew, and the control effect against cucumber downy mildew is especially remarkable.

Formulation Preparation Examples 1-2

This embodiment is provided to describe the preparation of 30 wt % wettable powder.

The constituents are mixed sufficiently in the following proportions, and the obtained mixture is pulverized in a super-fine pulverizer; thus, 30 wt % wettable powder is obtained.

| | |
|---|---|
| Compound Y14078 or Y14079: | 30% |
| Sodium dodecyl sulfate: | 2% |
| Sodium lignosulfonate: | 3% |
| Naphthalene sulfonic acid-formaldehyde condensate: | 5% |
| Light catcium carbonate: | to make up to 100% |

Formulation Preparation Examples 3-4

This embodiment is provided to describe the preparation of 40 wt % suspension.

The constituents are mixed sufficiently in the following proportions; thus, 40 wt % suspension is obtained.

| | |
|---|---:|
| Compound Y14078 or Y14079: | 40% |
| Ethylene glycol: | 10% |
| Nonylphenol polyethylene glycol ether: | 6% |
| Sodium lignosulfonate: | 5% |
| Carboxymethyl cellulose: | 1% |
| 37% formaldehyde solution: | 0.2% |
| 75% silicone oil emulsion: | 0.8% |
| Water: | to make up to 100% |

Formulation Preparation Examples 5-6

This embodiment is provided to describe the preparation of 60 wt % water dispersible granule.

The constituents are mixed in the following proportion, and then the mixture is pulverized; next, water is added into the mixture and the mixture is kneaded, and then is loaded into a pelletizer with a 10-100 mesh sieve screen and pelleted, and then dried and filtered; thus, 60 wt % water dispersible granules are obtained.

| | |
|---|---:|
| Compound Y14078 or Y14079: | 60% |
| Naphthalene sulfonic acid-formaldehyde condensate: | 12% |
| Sodium N-methyl-N-oleoyl taurate: | 8% |
| Polyvinyl pyrrolidone: | 2% |
| Carboxymethyl cellulose | 2% |
| Kaolin: | to make up to 100%. |

Test Case 3

The formulation obtained in the formulation preparation example 1-6 is prepared with water containing 1% Tween 80 into formulation in which the concentration of the active compound is 200 mg/L, and the formulation is tested against *Pseudoperonospora cubensis* with the method described in the test case 2. The result indicates: at 200 mg/L concentration of active compound, all of the formulations obtained in the preparation examples 1-6 achieve a 100% control effect against *Pseudoperonospora cubensis*.

While some preferred embodiments of the present invention are described above, the present invention is not limited to the details in those embodiments. Those skilled in the art can make modifications and variations to the technical scheme of the present invention, without departing from the spirit of the present invention. However, all these modifications and variations shall be deemed as falling into the scope of protection of the present invention.

In addition, it should be noted that the specific technical features described in above embodiments can be combined in any appropriate form, provided that there is no conflict. To avoid unnecessary repetition, the possible combinations are not described specifically in the present invention.

Moreover, different embodiments of the present invention can be combined freely as required, as long as the combinations don't deviate from the ideal and spirit of the present invention. However, such combinations shall also be deemed as falling into the scope disclosed in the present invention.

The invention claimed is:

1. A fungicidal compound in a structure represented by formula (II):

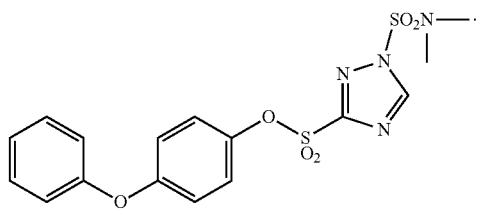

2. A fungicide composition, wherein its active ingredient comprises a compound in a structure represented by formula (II):

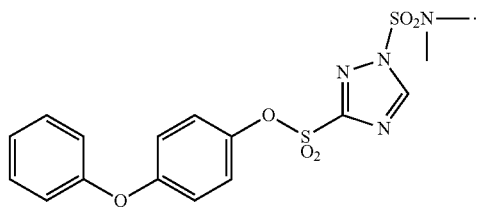

3. The fungicide composition according to claim 2, wherein the amount of the active ingredient in the fungicide composition is 1-95 wt %.

4. The fungicide composition according to claim 3, wherein the amount of the active ingredient in the fungicide composition is 5-80 wt %.

5. The fungicide composition according to claim 2, further comprising surfactant(s) and carrier(s) acceptable in a pesticide formulation.

6. A method of controlling cucumber downy mildew and/or rice sheath blight in a plant comprising applying the fungicide composition according to claim 2 to the plant or a plant growth location.

7. A preparation comprising the fungicide composition according to claim 2, wherein the formulation of the preparation is an emulsifiable concentrate, aqueous emulsion, microemulsion, soluble liquid, water suspension, suspension emulsion, ultra low volume spray, oil suspension, microcapsule suspension, surface spreading oil, wettable powder, water dispersible granule, dry flowable, soluble powder, soluble granule, emulsifiable powder, emulsifiable granule, pelletized granule, solid micro-capsule, effervescent tablet, effervescent granule, water floating dispersible granule, or seed coating agent.

8. A method of controlling cucumber downy mildew and/or rice sheath blight in a plant comprising applying the preparation according to claim 7 to the plant or a plant growth location.

9. The method according to claim 6, wherein the amount of the active ingredient in the fungicide composition is 1-95 wt %.

10. The method according to claim 9, wherein the amount of the active ingredient in the fungicide composition is 5-80 wt %.

11. The method according to claim 6, wherein the fungicide composition further comprising surfactant(s) and carrier(s) acceptable in a pesticide formulation.

12. The preparation according to claim 7, wherein the amount of the active ingredient in the fungicide composition is 1-95 wt %.

13. The preparation according to claim 12, wherein the amount of the active ingredient in the fungicide composition is 5-80 wt %.

14. The preparation according to claim 7, wherein the fungicide composition further comprising surfactant(s) and carrier(s) acceptable in a pesticide formulation.

\* \* \* \* \*